United States Patent
Grisel

(10) Patent No.: US 10,395,771 B2
(45) Date of Patent: Aug. 27, 2019

(54) COMPUTER-AIDED TELEMEDICAL EVALUATION

(71) Applicant: Das Wächter, LLC., Hoschton, GA (US)

(72) Inventor: George Robert Grisel, Hoschton, GA (US)

(*) Notice: Subject to any disclaimer, the term of this patent is extended or adjusted under 35 U.S.C. 154(b) by 142 days.

(21) Appl. No.: 15/453,239

(22) Filed: Mar. 8, 2017

(65) Prior Publication Data
US 2017/0262599 A1     Sep. 14, 2017

Related U.S. Application Data

(60) Provisional application No. 62/305,106, filed on Mar. 8, 2016.

(51) Int. Cl.
| | |
|---|---|
| *A61B 5/00* | (2006.01) |
| *A61B 5/11* | (2006.01) |
| *G16H 50/20* | (2018.01) |
| *G06F 19/00* | (2018.01) |

(Continued)

(52) U.S. Cl.
CPC .......... *G16H 50/20* (2018.01); *A61B 5/0013* (2013.01); *A61B 5/0022* (2013.01); *A61B 5/0077* (2013.01); *A61B 5/112* (2013.01); *A61B 5/1128* (2013.01); *A61B 5/7246* (2013.01); *A61B 5/7282* (2013.01); *A61D 99/00* (2013.01); *G06F 19/00* (2013.01); *G06F 19/321* (2013.01);

(Continued)

(58) Field of Classification Search
CPC ... G16H 50/20; G06F 19/3418; G06F 19/321; A61B 5/0013; A61B 5/112; A61B 5/1128; A61B 5/7246; A61B 5/7282; A61B 2503/40

See application file for complete search history.

(56) References Cited

U.S. PATENT DOCUMENTS

| | | | |
|---|---|---|---|
| 6,231,527 | B1 | 5/2001 | Sol |
| 2010/0179454 | A1 | 7/2010 | Davies |
| 2012/0274442 | A1 | 11/2012 | Mottram |

(Continued)

OTHER PUBLICATIONS

International Search Report for related international application No. PCT/US2017/021322, filed Mar. 8, 2017, dated Sep. 14, 2017.

*Primary Examiner* — Devin B Henson
(74) *Attorney, Agent, or Firm* — Thomas | Horstemeyer, LLP; Jason M. Perilla

(57) ABSTRACT

Computer-aided telemedical evaluation is described. A computing environment can receive a video comprising frames of a subject in motion. The computing environment can identify one or more anatomical features of the subject and determine one or more gait cycle patterns for the anatomical features by tracking motion of the anatomical features over a number of frames of the video. The computing environment can also examine the gait cycle patterns to identify symmetry, asymmetry, and other characteristics in the gait cycle patterns with respect to each other, the anatomical features of the subject, and/or inanimate features of the surroundings. Based on the examination, the computing environment can also provide an evaluation of the subject in the video. The evaluation can include the identification of one or more limbs associated with lameness in the subject. Care can then be administered to the subject, in part, based on the evaluation.

20 Claims, 7 Drawing Sheets

(51) Int. Cl.
  *A61D 99/00*   (2006.01)
  *A61D 17/00*   (2006.01)
(52) U.S. Cl.
  CPC ...... *G06F 19/3418* (2013.01); *A61B 2503/40* (2013.01); *A61B 2576/00* (2013.01); *A61D 17/00* (2013.01)

(56) References Cited

U.S. PATENT DOCUMENTS

| | | |
|---|---|---|
| 2013/0324888 A1 | 12/2013 | Solinsky |
| 2015/0196231 A1* | 7/2015 | Ziaie ................ A61B 5/112 600/595 |
| 2016/0073614 A1* | 3/2016 | Lampe ............... A01L 11/00 600/408 |

* cited by examiner

COMPUTER-AIDED TELEMEDICAL EVALUATION

CROSS-REFERENCE TO RELATED APPLICATIONS

This application claims the benefit of U.S. Provisional Application No. 62/305,106, filed Mar. 8, 2016, the entire contents of which is hereby incorporated herein by reference.

BACKGROUND

Proper healthcare can benefit from the timely analysis of the conditions of a subject or patient. Depending upon the particular needs of a subject, however, it can be relatively difficult to find the correct physician or medical practitioner to make a proper diagnosis. Particularly for animals, it can be relatively difficult, time consuming, and costly to find a suitable veterinary physician that specializes in the correct field of veterinary medicine to treat certain diseases, disorders, and injuries in animals. In that context, telemedicine involves the remote assessment of subjects by means of telecommunications technology. In many cases, the use of telemedicine for the remote evaluation of subjects can save time and costs.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1:
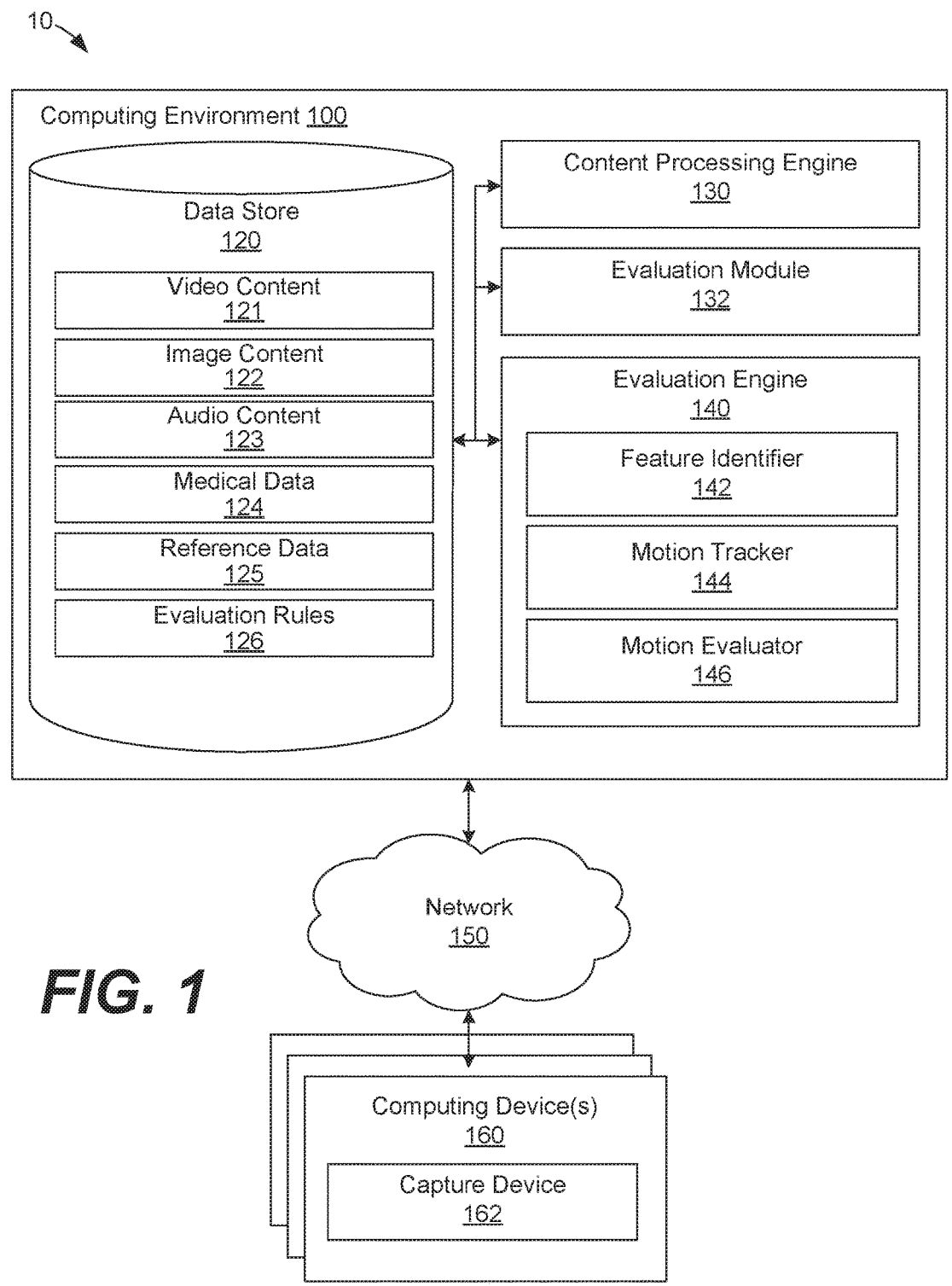
FIG. 1 illustrates a networked environment for the telemedical evaluation of subjects according to an example embodiment described herein.

In some cases, a visual analysis can be part of an assessment of certain disorders in various subjects, including animals. In some cases, however, the subject may be some distance from veterinarians or other healthcare service providers. This can result in long travel times for the subject or the veterinarian and the delayed assessment of various conditions related to the health and wellbeing of the subject. In some situations, the health condition, size, disposition, or other characteristics of a subject can hinder or delay the ability to transport it. At the same time, the delayed assessment of the health condition of the subject can result in prolonged or aggravated injuries. Therefore, assessment by direct observation may not be preferable or possible in many cases.

In the healthcare practice, information acquired through telemedicine can be used to provide healthcare at a distance. Telemedicine involves the remote assessment of a subject by means of telecommunications technology. In many cases, the use of telemedicine for the remote assessment of subjects can save time and costs. For example, the use of telemedicine can offer the elimination of physical risk to veterinary personnel, the reduction in veterinarian evaluation time and expense, synchronized networking between caretakers, and the increased accessibility to a centralized pool of medical expertise.

In telemedical practices for animals, a video of a subject animal standing, walking, trotting, or running in stride can be sent to a veterinarian for assessment. The veterinarian can watch the video to look for signs of lameness, for example, or other health-related problems or conditions. As used herein, gait is related to the manner of stance or movement of a subject, and lameness is related to any abnormality or deviation from the normal or expected gait of the subject. In other words, lameness is an indicator of an abnormal gait or stance of a subject. Lameness is often caused by pain but can be due to a dysfunction of the locomotor system, including neurologic and/or mechanical dysfunctions. As compared to an assessment by way of direct observation, however, it can be relatively difficult for a veterinarian to ascertain whether the animal exhibits any particular signs of lameness by observation of the video. For example, the quality of the video can be relatively poor due to capture at low resolution, capture with an unsteady hand, capture of the subject for a relatively short period of time, or capture of the video with too much or too little of the subject within any given video frame. Further, the expertise and experience of each veterinarian varies, and it can be relatively difficult to find a veterinarian with sufficient experience to identify various conditions, including lameness, of a subject by direct observation, let alone by observation of a video of the animal.

To identify potential sources, causes, or locations of lameness and other conditions, the embodiments described herein can automate lameness evaluation using a combination of various forms of telemedical data, such as videos, still images, audio recordings, and other medical data. Medical data can include a medical history of the subject, such as past diagnoses or past biological parameters including, but not limited to, heart rate, temperature, blood pressure, etc. Medical data can also include recently collected biological parameters.

As one example, an individual can record a video of a horse walking, trotting, or running using a computing device. The video can be transferred over a computer network to another computing environment for analysis. Automatically and/or at the direction of an individual, the video can be analyzed by an evaluation engine executing on the computing environment using image processing techniques. In one embodiment, the computing environment can identify one or more anatomical features of the subject and determine one or more gait cycle patterns for the anatomical features by measuring and/or tracking motion of the anatomical features over a number of frames of the video. The computing environment can also examine the gait cycle patterns to identify symmetry, asymmetry, and other characteristics in the gait cycle patterns with respect to each other and the anatomical features of the subject. Based on the examination of the gait cycle patterns, the computing environment can also provide an evaluation of the subject in the video. The evaluation can include the identification of one or more limbs associated with lameness in the subject. Care can then be administered to the subject, in part, based on the results of the evaluation.

While the concepts described herein reference a horse as one example subject that can be evaluated, the concepts can be used to more accurately identify potential sources of lameness in various subjects, including humans, cattle, sheep, pigs, goats, and other livestock, dogs, cats, and other animals. The concepts can help caretakers identify potential health problems to more quickly and efficiently tend to the needs of a subject without the need for time consuming or costly travel. Also, individuals can evaluate conditions more confidently by reference to the analysis conducted by the lameness evaluation systems and methods described herein.

Turning to the drawings, FIG. 1 illustrates a networked environment 10 for the telemedical evaluation of subjects according to an example embodiment described herein. The networked environment 10 includes a computing environment 100, a network 150, and a computing device 160. The computing environment 100 can be embodied as one or more computers, computing devices, or computing systems. In certain embodiments, the computing environment 100 can include one or more computing devices arranged, for example, in one or more server or computer banks. The computing device or devices can be located at a single installation site or distributed among different geographical locations. Although not shown in FIG. 1, the computing environment 100 can include one or more input/output devices, such as keyboards, cursor input devices, display screens, speakers, etc., to receive input from users, present video and audio, display evaluation reports, etc. As further described below, the computing environment 100 can also be embodied, in part, as certain functional or logical (e.g., computer-readable instruction) elements or modules as described herein.

The computing environment 100 can function as a telemedical evaluator of various subjects based on data obtained from sources including the computing device 160, among others. In that context, the computing environment 100 includes a data store 120, a content processing engine 130, an evaluation module 132, and an evaluation engine 140. The evaluation engine 140 includes a feature identifier 142, a motion tracker 144, and a motion evaluator 146.

The network 150 can include the Internet, intranets, extranets, wide area networks (WANs), local area networks (LANs), wired networks, wireless networks, cable networks, satellite networks, other suitable networks, or any combinations thereof. As one example, the computing environment 100 and the computing device 160 can be respectively coupled to one or more public or private LANs or WANs and, in turn, to the Internet for communication of data among each other. Although not shown in FIG. 1, the network 150 can also include communicative connections to any number and type of network hosts or devices, such as website servers, file servers, cloud computing resources, databases, data stores, or any other network or computing architectures.

In the networked environment 10, the computing environment 100 and the computing device 160 can communicate data between each other using one or more network transfer protocols or interconnect frameworks, such as hypertext transfer protocol (HTTP), simple object access protocol (SOAP), representational state transfer (REST), real-time transport protocol (RTP), real time streaming protocol (RTSP), real time messaging protocol (RTMP), user datagram protocol (UDP), internet protocol (IP), transmission control protocol (TCP), other protocols and interconnect frameworks, and combinations thereof.

The computing device 160 is representative of one or more computing devices. The computing device 160 can be embodied as any computing device, processing circuit, or processor based device or system, including a desktop computer, laptop computer, tablet computer, personal digital assistant, cellular telephone, or camera or video camera, among other example computing devices and systems. Depending upon its primary purpose or function, for example, the computing device 160 can include various peripheral devices or components. The peripheral devices can include input or communications devices or modules, such as keyboards, keypads, touch pads, touch screens, microphones, cameras, wireless communications modules (e.g., infra-red, WI-FI, or BLUETOOTH®), buttons, switches, or sensors. The peripheral devices can also include a display, indicator lights, speakers, global positioning system (GPS) circuitry, accelerometers, gyroscopes, or other peripheral devices depending upon the primary purpose or function of the computing device 160.

As shown in FIG. 1, the computing device 160 includes a capture device 162. Among other capture devices, the capture device 162 can be embodied as a camera, video camera, microphone, or other related device or combination thereof. The capture device 162 can also include one or more peripheral tools, medical instruments, or related devices to measure one or more biological parameters of a subject, such as heart rate, temperature, blood pressure, or other biological parameters. In one example, the capture device 162 can include a combination of a video camera, heart rate monitor, and blood pressure monitor. The heart rate and blood pressure monitors can be applied to a subject to collect data while a video of the subject moving is concurrently captured by the computing device 160.

The capture device 162 can be integrated with the computing device 160 or a peripheral component of the computing device 160. In any case, the capture device 162 can be used to capture various types of data for telemedical evaluation by the computing environment 100. As examples of the types of data that can be captured, the capture device 162 can be used to capture images, video, and/or audio of one or more subjects standing, walking, trotting, or running for telemedical evaluation by the computing environment 100. The data can be captured from various angles and/or fields of view over various periods of time, with or without the capture device 162 moving during capture. Video of the subject can be captured while the capture device 162 is stationary and the subject passes through the field of view of the capture device 162. Additionally or alternatively, the capture device 162 can capture data while a subject is within the field of view of the capture device 162, and the capture device 162 can be panned, moved, or rotated to maintain the subject within the field of view of the capture device 162 over a period of time.

As more particular examples of the types of images and/or video of subjects that can be captured by the capture device 162, images can be captured with the subject standing squarely on a level surface, dorsal views of the thoracic feet and limbs together, plantar views of the pelvic feet and limbs together, lateral views of each thoracic and pelvic foot separately, and right and left lateral views of the entire subject. Videos can also be captured with the subject moving on hard (e.g., on asphalt, concrete, frozen or hardened ground, etc.) or soft (e.g., on thawed or relatively soft ground) surfaces, cranial and lateral (e.g., side) views of the subject walking, trotting, or running in a straight line on a loose lead.

Once such data is captured by the capture device 162, it can be stored in local memory of the computing device 160 and transferred over the network 150 to the computing environment 100 for telemedical evaluation. When the data is received by the computing environment 100, it can be stored as the content 121-123 and evaluated by the content processing engine 130, the evaluation module 132, and the evaluation engine 140 as described in further detail below.

Turning back to the components of the computing environment 100, the data store 120 includes areas in memory for storing various types of data. For example, the data store 120 can store various types of data content for evaluation, such as video content 121, image content 122, and audio content 123. The data store 120 can also store medical data 124, reference data 125, and evaluation data 126, among other data for reference and/or processing by the computing environment 100.

The video content 121 can include one or more videos each including a number of image frames that can be evaluated by the evaluation engine 140. For example, the video content 121 can include a video of a subject standing, walking, trotting, and/or running in stride recorded from a side view of the subject. The video content 121 can also include a video of a subject recorded from a front, back, top, or other (e.g., corner or perspective) view. The video content 121 can be captured by an individual using the capture device 162 of the computing device 160, for example, and transmitted to the computing environment 110 over the network 150.

Similarly, the image content 122 and the audio content 123 can, respectively, include still images and audio recordings that can be evaluated by the evaluation engine 140. The image content 122 and the audio content 123 can also be captured and recorded by the capture device 162 of the computing device 160 and transmitted to the computing environment 100 over the network 150.

The medical data 124 can include, for example, a medical history of one or more subjects, including subjects shown in the video content 121 and the image content 122 and recorded in the audio content 123. The medical data 124 can include various medical details related to past and present characteristics and/or medical conditions of the subjects, such as the species, breeds, genders, sizes, weights, heart rates, temperatures, blood pressures, etc., of the subjects exhibited in the video, image, and audio content 121-123 (collectively "the content 121-123").

The medical data 124 can also include medical details related to subjects as it was observed and recorded over one or more periods of time. For example, the medical data 124 can include biological parameters coordinated or indexed in time with the content 121-123. The medical data 124 can be recorded or collected in any suitable way using any suitable tools, medical instruments, or related devices, including the capture device 162 of the computing device 160. Thus, the medical data 124 can be measured, recorded, and collected by or through the computing device 160 (or peripheral tools or instruments of the computing device 160) and transmitted to the computing environment 100 over the network 150.

The reference data 125 can include data related to various subjects for evaluation by the evaluation module 132. The reference data 125 can include analytical metrics, such as static reference data (e.g., images or references of standing or still posture), motion reference data (e.g., references of gait signatures, gait cycle patterns, gait distance differentials, gait cycle periods, gait cycle frequencies, etc.), associated with one or more subjects. The reference data 125 can include also data other types of analytical metrics, such as biological parameter data. In some cases, the data can be gathered and/or generated by the evaluation engine 140 based on an analysis of the content 121-123. For example, the reference data 125 for a given subject can include one or more gait cycle patterns associated with certain anatomical features of the subject, as those anatomical features are identified by the feature identifier 142 of the evaluation engine 140 and tracked over time by the motion tracker 144 of the evaluation engine 140.

The reference data 125 can include various posture reference data and statistics, gait signatures, motion data, and/or motion metrics associated with subjects. In that context, gait signatures can include combinations of gait cycle patterns associated with anatomical features of subjects over time. The gait signatures can be developed by the evaluation engine 140 based on an analysis of the content 121-123, for example, and stored as the reference data 125. Various examples of gait cycle patterns and gait signatures are described in further detail below with reference to FIGS. 3A, 3B, and 4-6.

Referring to the reference data 125, the evaluation module 132 can reference one or more gait signatures of various subjects to perform telemedical evaluations. For example, the evaluation module 132 can compare a first gait signature of a subject developed by the evaluation engine 140 with a second gait signature of the subject developed by the evaluation engine 140, where the first and second gait signatures are developed with reference to different videos stored in the video content 121. Thus, the reference data 125 can include a number of different types of analytical metrics, such as gait signatures, determined from the content 121-123 by the evaluation engine 140 over time.

The reference data 125 can include certain metrics collected and/or developed for subjects when the subjects were healthy. The reference data 125 can also include metrics collected and/or developed for subjects when the subjects were injured. The reference data 125 can further include benchmark analytical metrics, such as benchmark posture, benchmark gait signatures, benchmark biological parameters, etc., for examination by the evaluation module 132 as references for comparison. Benchmark analytical metrics can include motions tracked from videos of healthy and/or lame subjects (including various types of lameness in various limbs), and hypothetical motions generated for evaluation purposes, among other motions.

The evaluation rules 126 can include, for example, a set of rules and/or metrics for evaluating the health of subjects to determine or diagnosis a likely source of lameness, for example, or other health aspects. The evaluation rules 126 can be associated with subjects individually or collectively. In other words, the evaluation rules 126 can be associated or applicable to a single subject, a collection of subjects, or a number of different subjects or species of subjects, particularly if the subjects share certain attributes such as gait cycle patterns or other attributes. The evaluation rules 126 can differ from subject to subject, species of the subjects, age of the subjects, weight and/or size of the subjects, and other relevant factors.

The evaluation rules 126 can include rules for determining a source or region of lameness in subjects based on an evaluation (e.g., the identification of symmetry, asymmetry, etc.) of one or more gait cycle patterns associated with anatomical features of a subject, as those features are identified and tracked over time by the evaluation engine 140. Similarly, the evaluation rules 126 can include rules for determining a source of lameness based on a comparison of different gait cycle patterns associated with different anatomical features of a subject, as those patterns are tracked over time by the evaluation engine 140 and stored in the reference data 125. The evaluation rules 126 can also include rules that determine a source, severity, and contributing factors (among other relevant characteristics) of lameness in subjects based on an analysis of the motion of anatomical features as compared with other, non-motion related benchmark values for anatomical features, such as deviations from benchmark heights or ranges of motion of subjects when standing, walking, trotting, running in stride, etc.

The evaluation module 132 can reference the rules defined in the evaluation rules 126 to perform a binary search algorithm to arrive at a logical conclusion regarding probable sources and characteristics of lameness and other health conditions. In other words, the evaluation rules 126 can define a set of rules to progress through a number of factors or questions to search for and characterize gait abnormalities and other health conditions. For example, the rules can direct the evaluation module 132 to first identify front and/or back end lameness in a subject, then determine a grade or severity of the lameness, then determine a nature of the lameness, then determine a right or left side limb associated with the front or back end lameness, then determine whether the lameness is influenced by direction of travel of the subject, and finally determine whether the lameness is influenced by the surface upon which the subject travels, etc. Such a binary search or decision algorithm can proceed in any suitable order and fashion as defined by the evaluation rules 126, which can vary from subject to subject.

The content processing engine 130 can be embodied as an interpreter, editor, and/or manipulator of the content 121-123, and can be embodied in hardware, software, or a combination of hardware and software. The content processing engine 130 is configured to manipulate certain aspects of the content 121-123, when applicable (and beneficial), to prepare the content 121-123 for visual evaluation by an individual on a display and/or for evaluation by the evaluation module 132 and the evaluation engine 140. For example, the content processing engine 130 can be relied upon to select, format, and condition the content 121-123 (or portions of the content 121-123) for analysis and evaluation by the evaluation engine 140. In that context, the content processing engine 130 can perform image stabilization on various frames of videos in the video content 121. For example, the content processing engine 130 can manipulate image frames of videos in the video content 121 to center and stabilize a subject shown in the video content 121 across a number of image frames.

The content processing engine 130 can also update levels of brightness and/or contrast on image frames of videos in the video content 121 and images in the image content 122, and enhance the sharpness of videos in the video content 121 and images in the image content 122. The content processing engine 130 can overlay multiple images in the image content 122, adjust the speed and/or direction of videos in the video content 121, mix or combine videos (or parts of videos) in the video content 121 and images (or parts of images) in the image content 122, edit the length of videos in the video content 121, upscale and downscale the numbers of pixels of videos in the video content 121, interpolate frames of videos in the video content 121, calculate metrics or measurements based on images and videos in the content 121-123, and perform other video and image processing tasks to prepare the content 121-123 for further processing and manipulation.

The evaluation module 132 is configured to evaluate data stored in the data store 120 to prepare telemedical evaluations of subjects. In that context, the evaluation module 132 can provide a report including metrics associated with various conditions related to the health and wellbeing of subjects. As one example, the evaluation module 132 can evaluate gait signatures of one or more subjects stored in the reference data 125 based on one or more rules stored in the evaluation rules 126 to provide an evaluation or interpretation of lameness associated with one or more limbs of the subjects. Reports generated by the evaluation module 132 can be stored in the data store 120, presented on a display for individuals, printed, e-mailed, etc. Individuals, such as veterinarians or other healthcare service providers, can reference the reports to determine an appropriate manner in which to assist subjects. The reports can be used as a secondary source to recognize lameness, confirm a diagnosis provided by a veterinarian, for example, or to tailor the protocols suggested by the veterinarian to assist subjects.

The evaluation module 132 is not limited to the mere identification of lameness, as it is also capable of identifying, as secondary queries, which regions or limbs of a subject that are lame, the nature of such lameness, the severity of such lameness, and which gaits are affected by the lameness. The evaluation module 132 can also determine the consistency of lameness, potential factors contributing to lameness, and certain distinguishable traits of the gait of a subject. To draw a conclusion on any secondary query, the evaluation module 132 can evaluate any number of different characteristics exhibited by subjects based on the data gathered from the content 121-123 by the evaluation engine 140.

As examples of the types of characteristics of subjects that can be evaluated by the evaluation module 132, the evaluation module 132 can evaluate whether subjects exhibit symmetry or asymmetry in movement between diagonal pairs of limbs; whether subjects exhibit any altered movement or orientation associated with the axial anatomy (e.g., head, neck, back); whether subjects exhibit dragging or falling movements, to which ends(s) subjects transfer weight, to which side(s) subjects transfer weight; whether subjects transfer weight to one side, limb, or pair of limbs to underload another side, limb, or pair of limbs; whether subjects transfer weight by dropping below and/or rising above typical levels in a gait cycles; whether lameness is weightbearing (e.g., on impact) or non-weightbearing (e.g., on push-off) in nature, etc.

The evaluation module 132 can also evaluate the extent or severity of various conditions, including lameness, based on the extent or degree to which deviations from typical levels in gait cycles occur, along with the consistency of such conditions. As for consistency, the evaluation module 132 can determine whether lameness is evident during every stride, on a regular (e.g., daily) basis, and/or in every environmental (e.g., surface type, temperature, etc.) circumstance. The evaluation module 132 can also evaluate which gaits are affected, such as standing, walking, trotting, pacing, cantering, galloping, racking, running and combinations thereof. In the context of the types of evaluations described herein, the evaluation rules can include a number of different rules by which to evaluate a number of different contributing factors to lameness. Further details related to the operation of the evaluation module 132 are described below.

As noted above, the evaluation engine 140 includes the feature identifier 142, the motion tracker 144, and the motion evaluator 146. Overall, the evaluation engine 140 is configured to provide the evaluation module 132 with a set of refined data or metrics (e.g., motion data and/or metrics) by which to perform evaluations. Before turning to a more detailed description with reference to FIG. 2, the feature identifier 142 is configured to identify one or more anatomical features or markers (collectively "features") associated with subjects in one or more image frames of videos or still images from the content 121-123. The motion tracker 144 is configured to track one or more of the features identified by the feature identifier 142 as they move over time, for example, between, frames in video or image files of the video content 121. In doing so, the motion tracker 144 can generate motion data, including gait signatures, gait cycle patterns, gait distance differentials, gait cycle periods, gait cycle frequencies, etc., associated with one or more subjects.

Before turning to a more detailed description with reference to FIGS. 3A, 3B, and 4-6, the motion evaluator 146 is configured to analyze the motion data generated by the motion tracker 144. Thus, the motion evaluator 146 can compare and evaluate various gait signatures, gait cycle patterns, gait distance differentials, gait cycle periods, gait cycle frequencies, etc., associated with one or more subjects. By evaluating the motion data from the motion tracker 144, the motion evaluator 146 can provide data to the evaluation module 132 for evaluation. As one example, the motion evaluator 146 can identify asymmetry in one or more gait cycle patterns of a subject, which may be an indicator of lameness to the evaluation module 132.

Figure 2:
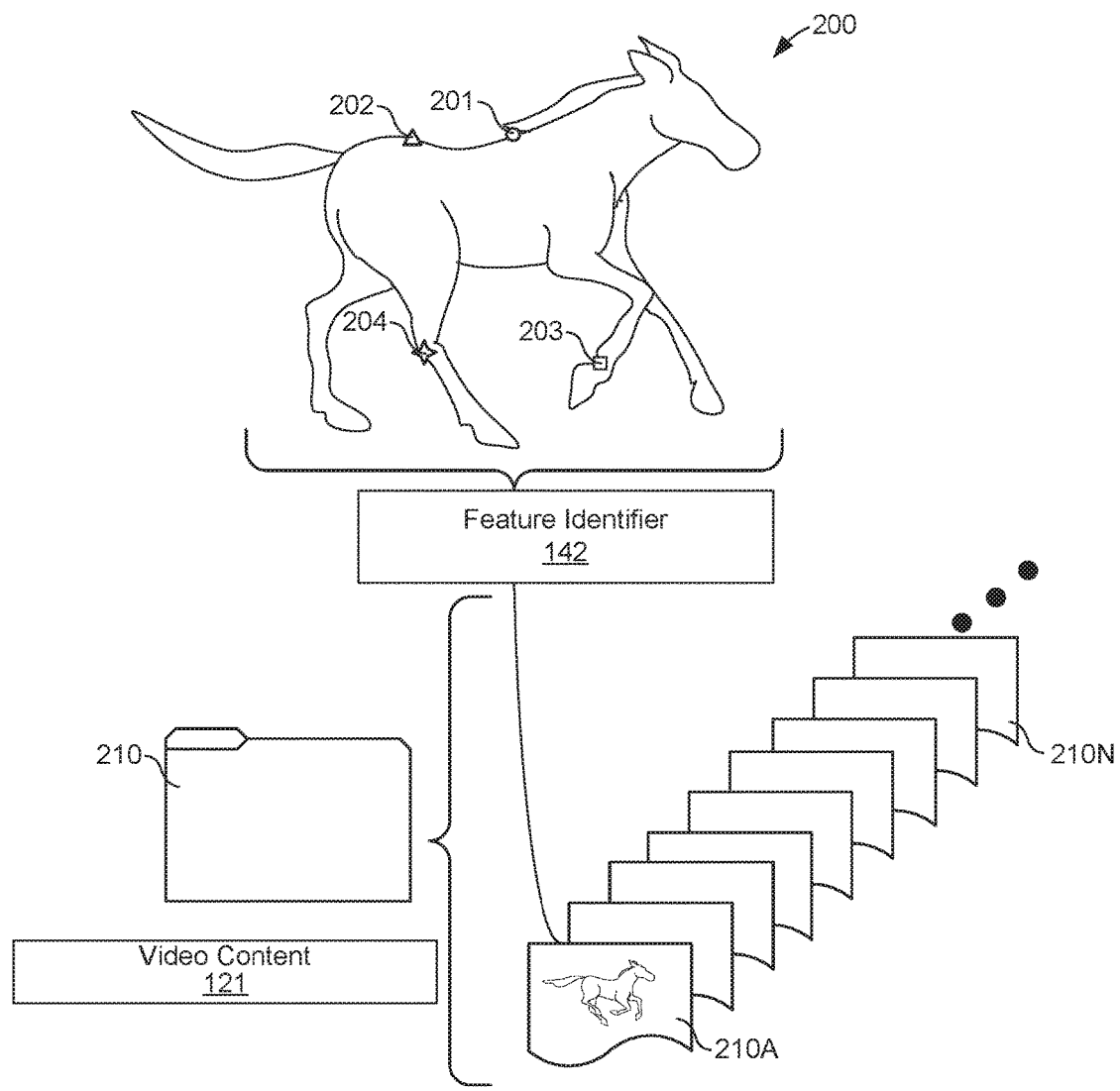
FIG. 2 illustrates example features of an example subject that can be identified according to example embodiments described herein.

To further describe the operations of the evaluation engine 140, FIG. 2 illustrates example features of an example subject 200 that can be identified by the feature identifier 142. Although FIGS. 2, 3A, 3B, and 4-6 are described and illustrated with the subject 200 shown as a horse, the concepts described herein are applicable to the computer-aided telemedical evaluation of other subjects, including other animals and humans. In other words, the concepts of feature identification, motion tracking, and motion evaluation can be applied similarly to other subjects, and the embodiments are not limited to use with any particular species of subjects.

As shown in FIG. 2, the subject 200, which is a horse in this case, is present in image frames 210A-210N of a video file 210 stored in the video content 121. In this example, the video file 210 includes a video of the subject 200 in motion, and the video file 210 was captured to show the subject 200 from its side. The feature identifier 142 is configured to analyze a number of the image frames 210A-210N to identify one or more features of the subject 200. The feature identifier 142 can identify features of the subject 200, for example, by processing one or more of the of the image frames 210A-210N of videos or still images in the content 121-123 using image pixel-level processing techniques described herein or known in the field. The feature identifier 142 can also identify features based on contrast and/or shape comparisons with known shapes, colors, contrasts, textures, or other identifying characteristics of the features in the reference data 125.

In the example provided in FIG. 2, the feature identifier 142 has identified the features 201-204, which correspond, respectively, to the withers, croup, right fetlock, and right hock of the subject 200. The embodiments are not limited to the identification of any particular features of any particular subjects, however, and the withers, croup, right fetlock, and right hock of the subject 200 are provided as representative examples of the types of features that can be identified by the feature identifier 142. Other features of the subject 200 can be identified, such as the nose, ears, eyes, poll, pastern, tuber sacrale, hoof, back, etc. of the subject 200 or other subjects, including humans.

In some cases, the feature identifier 142 can identify a species of a subject in the content 121-123 as part of the identification process with reference to data stored in the reference data 125. For example, the reference data 125 can include silhouettes of various subjects, and the feature identifier 142 can identify a species of the subject 200 based on reference silhouettes of various subjects. In turn, based on the species of the subject 200, the feature identifier 142 can be directed to identify one or more anatomical features associated with the species of the subject 200. Thus, if the subject 200 were a human, the feature identifier 142 might search for the head, wrists, elbows, knees, ankles, or other features of the human.

The feature identifier 142 can identify features of the subject 200 using any suitable pixel-level feature detection processing algorithms described herein or known in the field. Once features are identified by the feature identifier 142, positions of the features of can be recorded and saved in the data store 120. Positions of features can be identified, for example, and defined as pixel position coordinates in image frames in the video content 121 and/or the image content 122. In some cases, the positions of features can be identified using a relative or absolute coordinate system normalized using pixel locations, distances (e.g., inches, feet, etc.), or other relative or absolute metrics.

The feature identifier 142 can use a combination of edge, point, corner, region, or other feature detection algorithms to identify features of the subject 200 among a number of the image frames 210A-210N. In that context, edges can be detected at the boundaries between two regions of an image, as identified by an abrupt change in color, contrast, brightness, etc. In some cases, edges can be identified in images along pixel interfaces having strong gradient magnitudes. The feature identifier 142 can track or link a number of high gradient pixel interfaces together to identify an edge. Corners can be identified as edges having relatively high levels or specific levels of curvature. Corners having a certain shape, size, or other characteristic can be identified as features.

The feature identifier 142 is not limited to the identification of natural or anatomical features of subjects. In some cases, the subject 200 can be fitted or marked with equipment (e.g., clothing, saddles, bridles, collars, etc.) or by stickers of various colors or exhibiting various patterns or marks, emblems, markers, etc. having certain shapes, colors, or other characteristics, and those elements can be identified by the feature identifier 142.

Figure 3A:
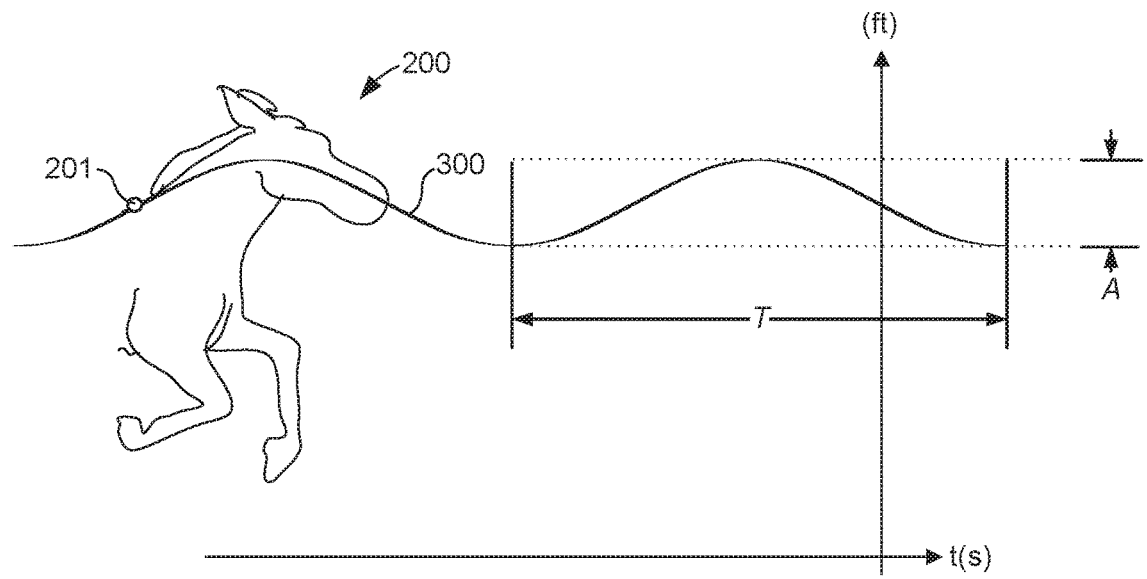
FIG. 3A illustrates a motion tracking example for a feature of the example subject identified in FIG. 2 according to example embodiments described herein.

Once identified by the feature identifier 142, the motion tracker 144 is configured to track one or more of the features 201-204 of the subject 200 as they move, frame to frame, between the image frames 210A-210N of the video file 210 or other content in the content 121-123. The motions of the features 201-204, as tracked by the motion tracker 144, can be stored in the data store 120 in an ongoing fashion over time. In that context, FIG. 3A illustrates a motion tracking example for the feature 201 of the subject 200 identified in FIG. 2. In FIG. 3A, the motion tracker 144 tracks the motion of the feature 201 to determine the gait cycle pattern 300 for the feature 201 of the subject 200 by tracking the motion of the feature 201 as it moves in the image frames 210A-210N of the video file 210 over time.

In various embodiments, motion data representative of the gait cycle pattern 300 can be stored by the motion tracker 144 in the data store 120 as a set of motion data points, each associated with a certain position (e.g., relative or absolute height, vertical position, etc.), with or without associated times or timestamps. Motion data for the gait cycle pattern 300 can also be stored as one or more functions (or combinations of functions) representative of the manner in which the feature 201 of the subject 200 moves over time. Such functions can define various amplitudes, periodicities, frequencies, and other characteristics of the gait cycle pattern 300 over time.

The motion data gathered and tracked by the motion tracker 144 can be associated with one or more dimensions, such as vertical or horizontal dimensions defined in pixels, inches, feet, time, etc. FIG. 3A illustrates the gait cycle pattern 300 in a coordinate plane with vertical and horizontal dimensions in units of feet. This can be accomplished by relating pixel positions in the image frames 210A-210N of the video file 210 with certain units according to one or more known references, such as a known height of the subject stored in the medical data 124, thereby associating the gait cycle pattern 300 to a metric of size or measure.

The motion data gathered and tracked by the motion tracker 144 can also be associated with one, two, or three spatial dimensions, and/or it can also be associated with time. In one embodiment, a third dimension of the motion data can be generated by the motion tracker 144 based on changes in size of the features 201-204 of the subject 200, to perceive depth. The third dimension can also be generated by the synchronization and analysis of more than one video of a subject, such as by one video captured from the side of the subject and another video captured from behind the subject.

The motion evaluator 146 can evaluate the gait cycle pattern 300 tracked by the motion tracker 144 to determine and/or define the amplitude, periodicity, frequency, and other characteristics of the gait cycle pattern 300 as they are exhibited over time. For example, the motion evaluator 146 can determine a period T of the gait cycle pattern 300. The motion evaluator 146 can also determine an amplitude A of the gait cycle pattern 300. The period T and the amplitude A are provided as representative examples of the types of characteristics of the gait cycle pattern 300 that can be determined by the motion evaluator 146 for analysis by the motion evaluator 146 and/or the evaluation module 132, as other characteristics can be determined. The characteristics tracked by the motion tracker 144 can be stored in the data store 120 and, thus, made accessible to the motion evaluator 146 and/or the evaluation module 132 for further processing.

To assist with motion tracking, the motion tracker 144 can reference a motion model in the reference data 125 that describes (at least in part) how certain features for a given subject might move over time. In that context, one or more motion models of certain features of subjects can be stored in the reference data 125 for reference by the motion tracker 144. For example, an example pattern of the withers of a horse trotting can be stored in the reference data 125, and it can be expected to adhere to certain characteristics. Based on a motion model that defines such a pattern of motion, the motion tracker 144 can work with the feature identifier 142 to track the motion of the withers across the image frames 210A-210N of the video file 210.

Figure 3B:
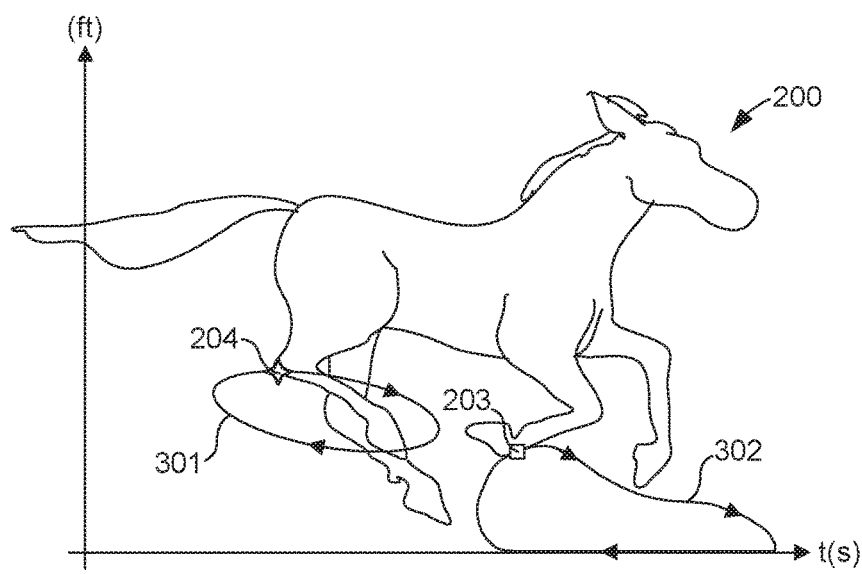
FIG. 3B illustrates another motion tracking example for features of the example subject identified in FIG. 2 according to example embodiments described herein.

The gait cycle pattern 300 shown in FIG. 3A is provided as one example, but the motion data gathered and tracked by the motion tracker 144 can take other forms. For example, FIG. 3B illustrates another motion tracking example for the features 203 and 204 of the subject 200 identified in FIG. 2. The gait cycle patterns 301 and 302 might be tracked and captured by the motion tracker 144 if the image frames 210A-210N in the video file 210 each exhibit the subject 200 in the center (or proximate center) of the image frames 210A-210N. In other words, patterns similar to the gait cycle pattern 300 can be generated when subjects cross the field of view of image frames in video files over time (e.g., if the capture device 162 was pointed steady in one direction while a subject passes over the field of view of the capture device 162).

On the other hand, the gait cycle patterns 301 and 302 can be generated in the case that subjects are present in the center (or proximate center) of the image frames of video files over time (e.g., if the capture device 162 was moved to maintain the subject within the field of view of the capture device 162 as the subject moves). In some cases, even if a subject crosses the field of view of image frames in a video, the content processing engine 130 can reposition the image frames to maintain the subject in a central position for processing.

Similar to the gait cycle pattern 300, the motion evaluator 146 can evaluate the gait cycle patterns 301 and 302 to determine and/or define the amplitude, periodicity, frequency, and other characteristics of the gait cycle patterns 301 and 302 as they are exhibited over time. The characteristics can be stored in the data store 120 and, thus, made accessible to the motion evaluator 146 and/or the evaluation module 132 for further processing. The gait cycle patterns 300-301 (and others illustrated in FIGS. 4-7) are representative and provided as examples for context. In practice, gait cycle patterns can have other shapes, sizes, and characteristics.

Figure 4:
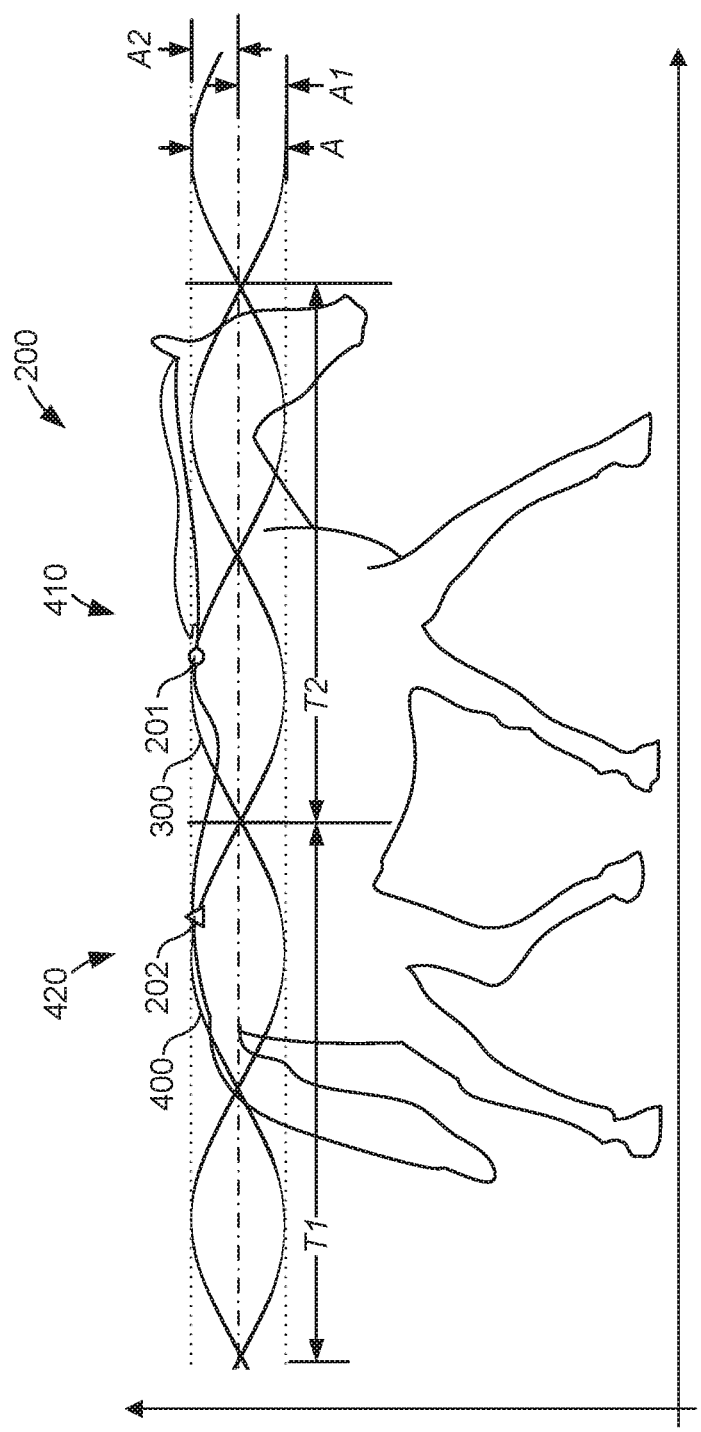
FIG. 4 illustrates another motion tracking example of the example subject identified in FIG. 2 according to example embodiments described herein.

FIG. 4 illustrates another motion tracking example of the example subject 200 identified in FIG. 2. In FIG. 4, the gait cycle pattern 300 for the feature 201 is shown along with the gait cycle pattern 400 for the feature 202, both of which can be tracked from the video file 210 (or other video file or combinations of video files) by the motion tracker 144 as described herein. As noted above, the feature 201 corresponds to the withers of the subject 200, and the feature 202 corresponds to the croup of the subject 200. Together, the gait cycle patterns 300 and 400 embody a gait signature of the subject 200. In addition to other characteristics, the motion evaluator 146 can evaluate the gait cycle patterns 300 and 400 for symmetry and/or asymmetry over one or more lengths of time (such as the period T, ½ the period T, ¼ the period T, or another suitable length of time).

With reference to FIG. 4, the symmetry of the gait cycle pattern 300 can be evaluated based on an analysis of the amplitude A of the gait cycle pattern 300 during the period T1 as compared to the amplitude A during the period T2. For example, the motion evaluator 146 could determine whether the amplitude A of the gait cycle pattern 300 is larger or smaller over the period T1 than over the period T2. If so, the gait cycle pattern 300 includes an asymmetry, which can be an indicator of lameness or other health issues in the front end 410 of the subject 200. Similarly, the motion evaluator 146 could determine whether the amplitude A of the gait cycle pattern 400 is larger or smaller over the period T1 than over the period T2, as an indicator of lameness or other health issues in the back end 420 of the subject 200. Such examples are described in further detail below with reference to FIG. 5.

In another example, the motion evaluator 146 could determine that the half amplitude A1 of the gait cycle pattern 300 is larger or smaller than the half amplitude A2. Alternatively, the motion evaluator 146 could determine that the half amplitude A1 of the gait cycle pattern 400 is larger or smaller than the half amplitude A2. Those types of asymmetry can be an indicator of other types of lameness or other health issues in the subject 200.

As described in further detail below, the motion evaluator 146 can also identify and compare regions of symmetry and asymmetry between the gait cycle patterns 300 and 400 and/or other gait cycle patterns, such as those associated with the nose, ears, eyes, poll, pastern, fetlocks, hocks, and other anatomical features of the subject 200. The motion evaluator 146 can also identify and compare regions of symmetry and asymmetry in gait cycle patterns associated with other, non-anatomical features identified for the subject 200 (and other subjects, including other animals and humans), such as features associated with equipment (e.g., clothing, saddles, bridles, collars, etc.), stickers, emblems, markers, etc. As one example described in further detail below with reference to FIG. 6, the motion evaluator 146 can compare regions of symmetry and asymmetry between the gait cycle pattern 300 and a gait cycle pattern of a fetlock of the subject 200, to ascertain whether lameness associated with the front end 410 of the subject 200 is attributable to a right or left front limb of the subject 200.

As compared to an assessment by way of observation of a video, the motion evaluator 146 is better suited to carefully measure and track motions exhibited in various gait cycle patterns shown in the video. Particularly, because the motion tracker 144 can develop and store motion data related to various gait cycle patterns along with position, size, and timing metrics associated with those patterns, the motion evaluator can make relatively precise measurements and comparisons. Thus, while it might be relatively difficult for a veterinarian to ascertain whether a subject exhibits a particular sign of lameness by observation of a video, the computer-aided telemedical evaluation embodiments described herein provide more accurate, reliable, and objective tools to evaluate the conditions of subjects.

Figure 5:
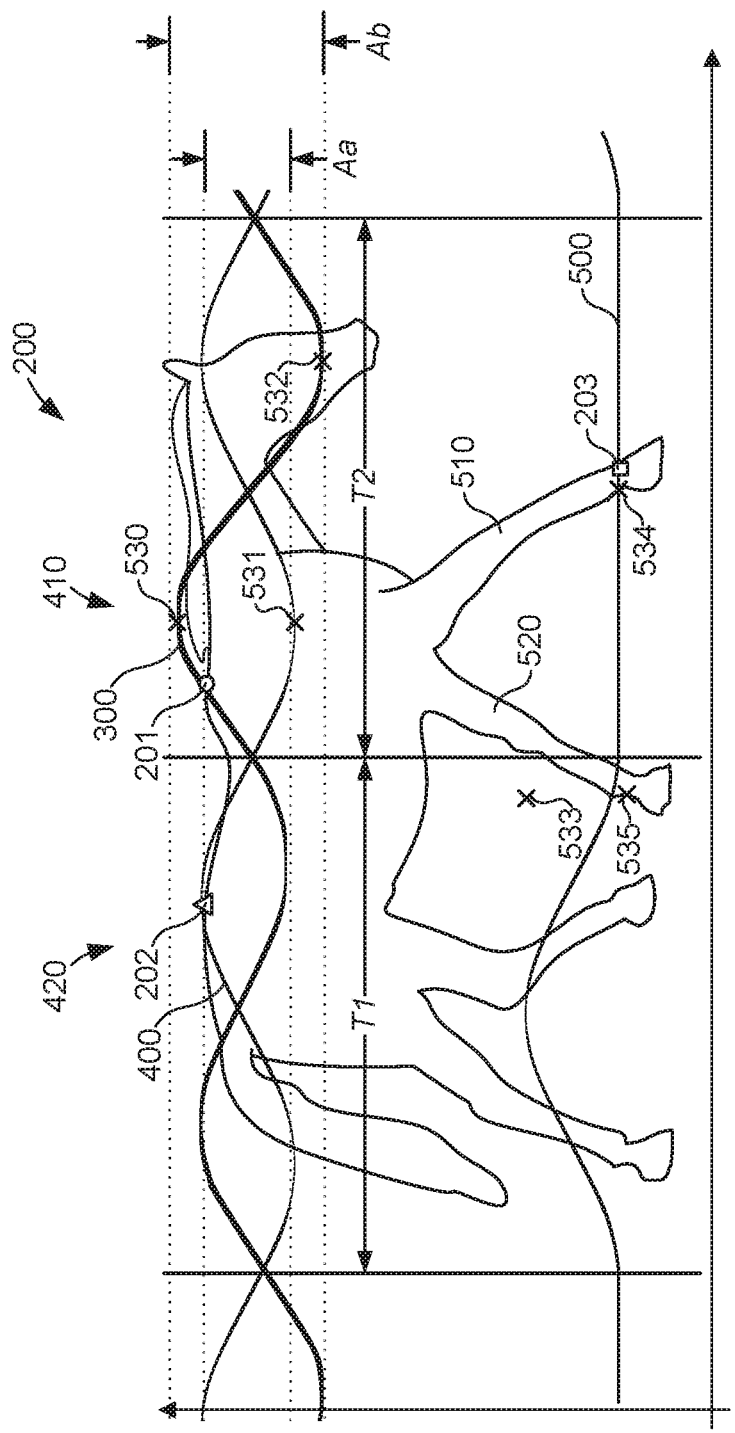
FIG. 5 illustrates another motion tracking example of the example subject identified in FIG. 2 according to example embodiments described herein.

Continuing to another example, FIG. 5 illustrates another motion tracking example of the subject 200 identified in FIG. 2 according to example embodiments described herein. In FIG. 5, the gait cycle patterns 300, 400, and 500 of the features 201-203, respectively, are shown. The feature 203 (i.e., the right fetlock of the subject 200) is associated with the right front limb 510 of the subject 200. Thus, the gait cycle pattern 500 is associated with the right front limb 510 of the subject 200.

Initially, the motion evaluator 146 can evaluate the gait cycle patterns 300 and 400 for symmetry and/or asymmetry over the periods T1 and T2, among others, to identify that the gait cycle pattern 300 includes an asymmetry over the period T2. Particularly, the gait cycle pattern 300 exhibits a larger amplitude Ab over the period T2 as compared to the amplitude Aa exhibited over the period T1. Because the gait cycle pattern 300 is attributed to motion tracking for the feature 201 (i.e., the withers of the subject 200), the evaluation module 132 can identify lameness in the front end 410 of the subject 200, as an initial evaluation of the subject 200, based on the asymmetry in the gait cycle pattern 300. Additionally, the evaluation module 132 can evaluate a severity of the lameness in the front end 410 of the subject 200 based on the value of the amplitude Ab, a comparison of the amplitude Ab with an expected benchmark amplitude stored in the reference data 125, or a comparison of the amplitude Aa with the amplitude Ab.

As a further evaluation of the subject 200, the motion evaluator 146 can compare the gait cycle pattern 300 to the gait cycle pattern 500. Particularly, the motion evaluator 146 can compare the gait cycle pattern 300 to the gait cycle pattern 500 to identify that the asymmetry in the gait cycle pattern 300 over the period T2 corresponds to a period in which the right front limb 510 of the subject 200 is in contact with the ground. Such a condition can be related to lameness in the left front limb 520 of the subject 200, and a rule to identify that condition can be stored in the evaluation rules 126 for reference by the evaluation module 132.

In cases of weight-bearing lameness, an injured limb may be favored while a healthy limb is relied upon more heavily to carry and displace weight. With reference to the example shown in FIG. 5, the subject 200 appears to favor (e.g., bears less weight on) the left front limb 520 because it is injured. To compensate for the injury to the left front limb 520, the movement of the subject 200 due to the right front limb 510 is more exaggerated (e.g., the right front limb 510 is relied upon more to carry and displace weight), and that exaggerated movement is exhibited in the larger amplitude Ab in the gait cycle pattern 300 over the period T2 as compared to the smaller amplitude Aa over the period T1.

With further examination of the gait cycle pattern 500, it is clear that the right front limb 510 is in contact with the ground over the period T1 and that the subject 200 relies upon the right front limb 510 more heavily. Thus, the evaluation module 132 can identify lameness in the front end 410 of the subject 200, as an initial evaluation of the subject 200, and further identify that the lameness is attributed (or likely attributed) to the left front limb 520 based on an examination of the gait cycle patterns 300 and 500.

Before continuing to other examples, it is noted that lameness in the back end 420 of the subject 200 can be identified by the motion evaluator 146 and/or the evaluation module 132 in a similar way, if asymmetry were found in the gait cycle pattern 400 rather than (or in addition to) the gait cycle pattern 300. Similarly, based on a gait cycle pattern of the feature 204 (FIG. 3B), for example, asymmetry in the gait cycle pattern 400 could be attributed to one of the right or left back limbs of the subject 200.

The manner in which the gait cycle patterns of the subject 200 are evaluated can be dependent upon various factors, and the description of the evaluation of the subject 200 in FIG. 5 is only one representative example. In other cases, if the subject were pacing, one or both of the gait cycle patterns 300 and 400 might be expected to be relatively flat. In that case, the motion evaluator 146 and the evaluation module 132 might focus more on the gait cycle pattern 500 to recognize conditions.

In other aspects of the embodiments, the motion evaluator 146 and the evaluation module 132 can identify and evaluate one or more gait locus points. A gait locus point can be any point or position identified in connection with a subject, as the subject is depicted or shown in the content 121-123. In FIG. 5, a number of example gait locus points 530-535 are identified. Gait locus points, including the example gait locus points 530-535, can be associated with features of subjects identified by the feature identifier 142. Further, each gait locus point can be associated by the motion tracker 144 with a certain position in space and time, and those positions and points in time can be stored in the data store 120.

In some cases, a gait locus point can be a point on or along a gait cycle pattern determined by the motion tracker 144. For example, the gait locus points 530 and 532 correspond to two different points in time along the gait cycle pattern 300, and the gait locus point 531 corresponds to another point in time along the gait cycle pattern 400. Although being associated with different points in time, the motion tracker 144 can define the positions of each of the gait locus points 530-532 based on a common coordinate system or set of spatial relationships. On that basis, the evaluation engine 140 can make spatial comparisons between the gait locus points 530-532 to identify lameness.

The evaluation module 132 can evaluate one or more of the gait locus points 530-532 to determine (or provide an indication of) various aspects of lameness of the subject 200. For example, the evaluation module 132 can identify that the gait locus point 532 is lower than the gait locus point 531, which can be an indicator of lameness. Additionally or alternatively, the evaluation module 132 can identify distances between any two or more of the gait locus points 530-532 as another indicator of lameness. Further, the evaluation module 132 can identify certain angles or other geometric metrics between two or more of the gait locus points 530-532 as other indicators of lameness.

However, it is not necessary that all gait locus points be associated with a gait cycle pattern. Instead, gait locus points can be determined by the feature identifier and/or motion tracker 144 without an associated gait cycle pattern being determined. In that context, it is noted that the evaluation engine 140 can evaluate various aspects of lameness in subjects with reference to one or more individual images in the image content 122. The relative or absolute positions of a number of gait locus points compared to each other or to other reference points (e.g., the ground, etc.) within one, two, or more individual photographs or image frames can also provide insight with regard to the motion of a subject.

For example, the maximum (or near maximum) stride height of the left front limb 520 of the subject 200 can be obtained by measuring the static distance between the gait locus point 533 (identified at the appropriate moment in time in some content) and the surface of the ground and/or the gait locus point 535. That distance can be compared to the distance representing the maximum height of right front limb 510 of the subject 200 (identified in a similar fashion at the appropriate moment in time in some other content). The differences in these heights might be an indication of lameness in the subject 200.

As another example, the total stride length of the right front limb 510 could be assessed by measuring the distance between the gait locus points 534 and 535 as the right front limb 510 contacts the ground surface at two different times. Each of the gait locus points 534 and 535 can be determined in respective images in the image content 122 and/or in respective image frames of a video in the video content 121. Alternatively, motion blur across a number of successive frames in a video can be used to measure the distance that one or more features travel over a period of time or between multiple points of contact with the ground, for example.

In another example, the evaluation module 132 can compare the stride lengths of various limbs to assess their relative distances at a moment that contralateral limbs are concurrently nearest to (or contact) the ground. A difference in the distance between left and right limbs when the right limb is forward as apposed to when the left limb is forward can be an indication of lameness. The aspect of the stride most affected by the lameness (whether it is the anterior portion or the posterior portion) could also be assessed using this method.

The evaluation module 132 can also measure, statically, abnormal posture or leaning with reference to images of subjects. Differences in the distance between comparable features on the left and right sides of the subject might indicate lameness. For example, the distance between the head and left hip versus the distance between the head and right hip of a human can be an indicator of lameness. The evaluation module 132 can assess leaning statically by measuring angles between features within a single image or image frame in a video. Further, excessive or inadequate leaning of the body relative to the ground surface while turning might indicate lameness.

Figure 6:
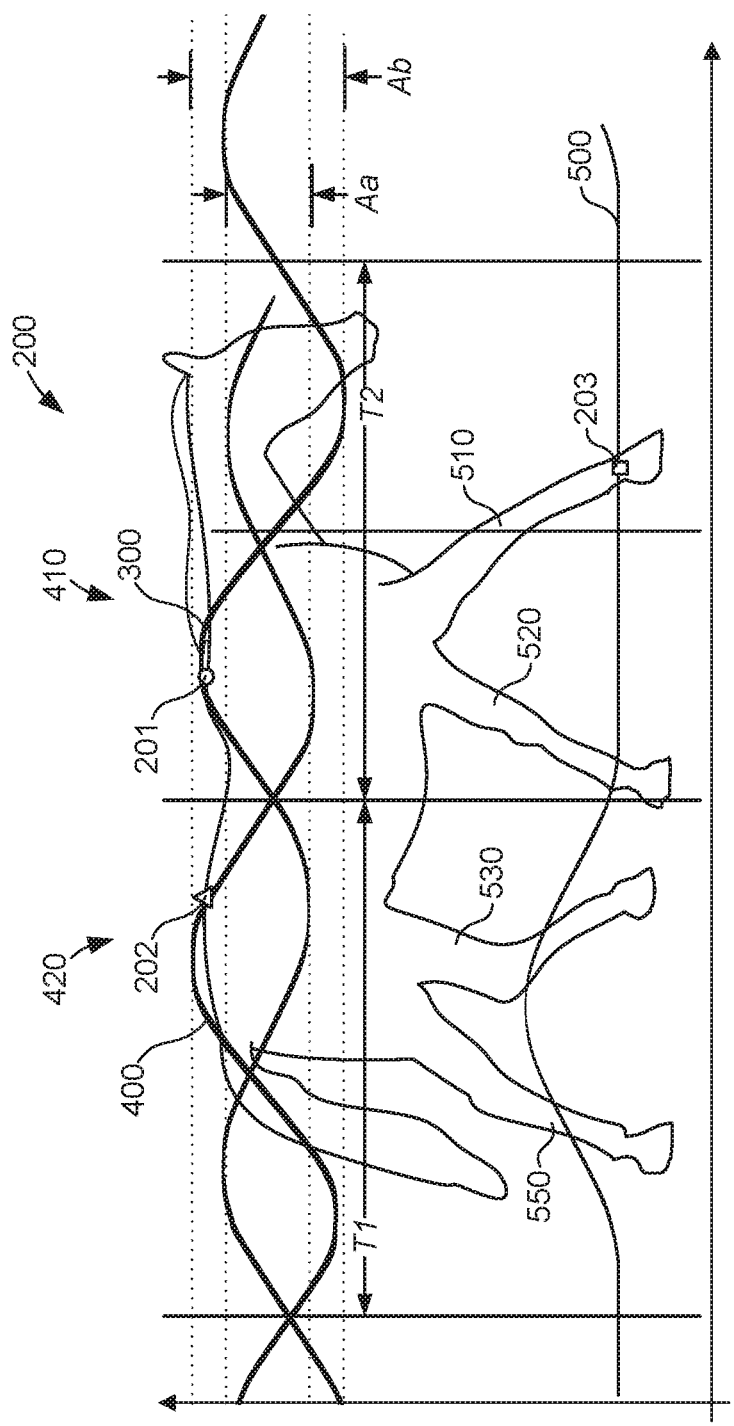
FIG. 6 illustrates another motion tracking example of the example subject identified in FIG. 2 according to example embodiments described herein.

FIG. 6 illustrates another motion tracking example of the subject 200 identified in FIG. 2 according to example embodiments described herein. In FIG. 6, the gait cycle patterns 300, 400, and 500 of the features 201-203, respectively, are shown. In this case, the motion evaluator 146 can examine the gait cycle pattern 300 for symmetry and/or asymmetry over the periods T1 and T2 to identify that the gait cycle pattern 300 includes an asymmetry over the period T2. Particularly, the gait cycle pattern 300 exhibits a larger amplitude Ab over the period T2 as compared to the amplitude Aa exhibited over the period T1. The motion evaluator 146 can also examine the gait cycle pattern 400 for symmetry and/or asymmetry over the periods T1 and T2, among others, to identify that the gait cycle pattern 400 includes an asymmetry over the period T1. That is, the gait cycle pattern 400 exhibits a larger amplitude Ab over the period T1 as compared to the amplitude Aa exhibited over the period T2.

Here, the evaluation module 132 can identify lameness in both the front end 410 and the back end 420 of the subject 200, as an initial evaluation of the subject 200, based on the asymmetries in the gait cycle patterns 300 and 400. As a further evaluation of the subject 200, the motion evaluator 146 can compare the gait cycle pattern 300 to the gait cycle pattern 500 to identify that the asymmetry in the gait cycle pattern 300 over the period T2 corresponds to a period in which the right front limb 510 of the subject 200 is in contact with the ground. Such a condition can be related to lameness in the left front limb 520 of the subject 200 as described above with reference to FIG. 5.

Further, because the right front limb 510 and the rear left limb 540 are diagonal and based on known mechanics of diagonal limbs of the subject 200, the rear left limb 540 can be expected to contact the ground at the same time as the right front limb 510. In other words, the gait cycle pattern of the rear left limb 540 (not shown in FIG. 6) would be expected to be similar to that of the right front limb 510. Thus, the evaluation module 132 can identify lameness in the front end 410 and the back end 420 of the subject 200, as an initial evaluation of the subject 200. The evaluation module 132 can further identify that the lameness of the front end 410 is attributed (or likely attributed) to the left front limb 520 for the same reasons as described above with reference to FIG. 5.

Additionally, the evaluation module 132 can identify that the lameness of the back end 420 is attributed (or likely attributed) to the right back limb 550 based on an examination of the gait cycle pattern 500, which is expected to be similar to that of the right front limb 510. That is, the rear left limb 540 is expected to contact the ground during the period of asymmetry in the gait cycle pattern 400 over the period T1 based on the gait cycle pattern 500. Alternatively, the gait cycle pattern of the rear left limb 540 can be directly tracked and evaluated by the motion tracker 144 and the motion evaluator 146. In any case, the evaluation module 132 can determine that the lameness in the back end 420 is attributed (or likely attributed) to the right back limb 550, which is not expected to contact the ground (and may be favored) during the period of asymmetry in the gait cycle pattern 400 over the period T1 based on a review of the gait cycle pattern 500. Thus, FIG. 6 presents an example of concurrent weightbearing lameness in opposite front and back limbs of the subject 200.

FIGS. 2-6 are representative, and the evaluation engine 140 and evaluation module 132 can identify other features, track other types of motions, and conduct other types of gait evaluations. For example, the evaluation module 132 and/or evaluation engine 140 can identify regular, asymmetric movement of the withers and regular, asymmetric movement of the croup of a horse, which suggests that both the front end and the back end of the horse are lame. If the right front and right back limbs are in contact with the ground as the withers and croup drop excessively, respectively, this pattern would suggest concurrent weightbearing lameness of both the left front and left hind limbs. One or more rules to identify this type of pattern can be stored in the evaluation rules 126 for reference by the evaluation module 132 and/or evaluation engine 140 to generate a telemedical evaluation. The rules can also specify that, if the lameness of both the left front and left hind limbs are weightbearing in nature, have approximately the same severity, and involve different diagonal pairs of limbs, it is probable that the left front lameness is an artificial product of the left hind lameness.

Based on information identified, tracked, evaluated, and stored by the evaluation engine 140, the evaluation module 132 is configured to provide an evaluation of a subject, possibly including the identification of likely sources of lameness or other health conditions of the subject. In some embodiments, the likely sources of lameness can be identified as being associated with certain anatomical features of the subject as described above, and those sources can be identified in one or more reports generated by the evaluation module 132.

The evaluation provided by the evaluation module 132 can be organized in any suitable fashion, such as in one or more reports. In one embodiment, the evaluation engine 140 can calculate a statistical similarity or deviation of one or more motions as compared to benchmark motions stored in the reference data 125. As described above, such benchmark motions can include one or more previously-stored motions exhibited by the same or different subjects, or motions developed specifically for the purpose of evaluation. In addition, the evaluation module 132 can determine a severity or grade of lameness or other conditions by considering the similarity to or difference from benchmark levels, for example.

Reports generated by the evaluation module 132 can be stored in the data store 120, presented on a display for individuals, printed, e-mailed, etc. Individuals, such as veterinarians or other healthcare service providers, can reference the reports to determine an appropriate manner in which to assist subjects. The reports can be used as a secondary source to recognize lameness, to confirm a diagnosis provided by a veterinarian, for example, or to tailor the protocols suggested by the veterinarian to assist subjects.

Figure 7:
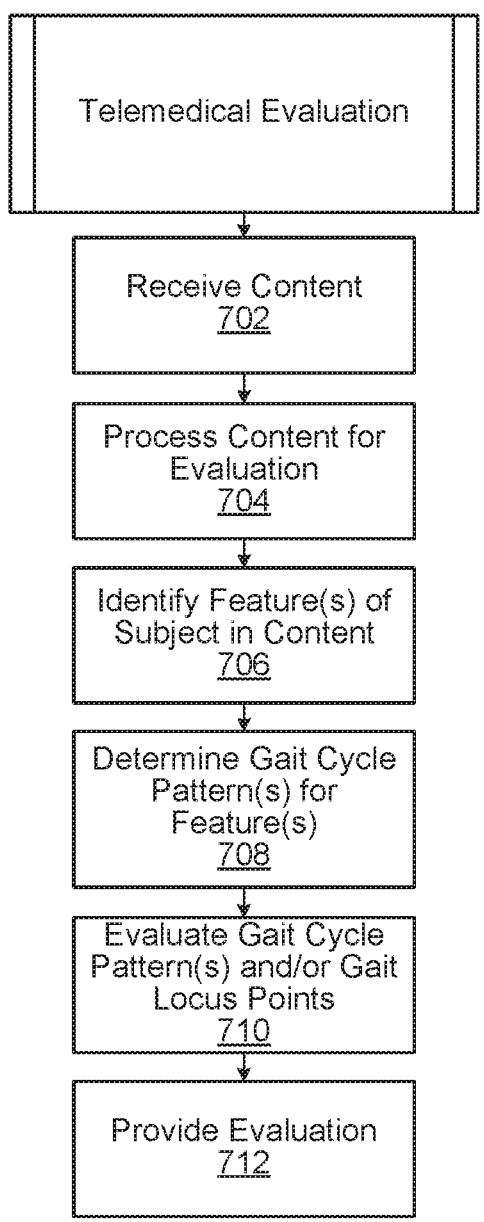
FIG. 7 illustrates an example process for telemedical evaluation according to example embodiments described herein.

FIG. 7 illustrates an example process for telemedical evaluation according to example embodiments described herein. The process can be performed by the computing environment 100 described with reference to FIG. 1, but other computing devices and environments can be relied upon to perform the process. The flowchart shown in FIG. 7 provides merely an example of the many different types of functional arrangements that may be employed to implement a process for telemedical evaluation according to embodiments described herein.

At step 702, the process includes the computing environment 100 receiving content for evaluation from the computing device 160, for example, over the network 150. The content can be stored as the content 121-123 and can include images, video, audio, etc., as described herein.

At step 704, the process includes the content processing engine 130 processing the content received at step 702. The processing can include manipulating certain aspects of the content 121-123 to prepare it for evaluation by an individual, the evaluation module 132, and/or the evaluation engine 140. The processing can include selecting, formatting, and conditioning the content 121-123 (or portions of the content 121-123) for analysis and evaluation. The processing can include performing image stabilization on the video content 121, centering and stabilizing a subject shown in the video content 121 across a number of image frames, altering levels of brightness and/or contrast of image frames in the video content 121 and the image content 122, and enhancing the sharpness of the video content 121 and the image content 122.

The processing can include overlaying multiple images in the image content 122, adjusting the speed and/or direction of the video content 121, mixing or combining videos (or parts of videos) in the video content 121 and images (or parts of images) in the image content 122, editing the length of videos in the video content 121, upscaling and/or downscaling the numbers of pixels in the video content 121, interpolating frames in the video content 121, calculating metrics or measurements based on images and videos in the content 121-123, and performing other video and image processing tasks to prepare the content 121-123 for further processing and manipulation.

At step 706, the process can include the feature identifier 142 identifying one or more features of a subject shown in the content received at step 702. The identifying can include a preliminary step of identifying a species of the subject as described herein. The identifying at step 706 is not limited to the identification of any particular features of any particular subjects. The features can include anatomical and non-anatomical (e.g., artificial) features. In later steps, the features can be related to gait locus points and/or used to determine gait cycle patterns. Further, the features can be used or referenced to provide static and/or motion-based assessments of lameness and other health conditions.

The identifying can include processing image frames of videos or still images in the content 121-123 using image pixel-level processing techniques described herein or known in the field. The feature identifier 142 can also identify features based on contrast and/or shape comparisons with known shapes, colors, contrasts, textures, or other identifying characteristics of the features in the reference data 125. Examples of the identification of features are provided above with reference to FIG. 2.

At step 708, the process includes the motion tracker 144 determining motion data related to the features identified at step 706. The motion data can include, among other data, gait cycle patterns for one or more of the features identified at step 706. As described above with reference to FIGS. 3A, 3B, and 4-6, the determining at step 708 can include tracking one or more features identified by the feature identifier 142 as they move over time, for example, between frames in video or image files of the video content 121. In that context, step 708 can also include the motion tracker 144 generating motion data, including gait signatures, gait cycle patterns, gait distance differentials, gait cycle periods, gait cycle frequencies, etc., associated with one or more subjects.

At step 710, the process includes the motion evaluator 146 evaluating the static and/or motion data determined at steps 706 and/or 708 to identify certain characteristics of the data that are suitable for and relevant to telemedical evaluation as described herein. For example, at step 710, the evaluating can include identifying symmetry or asymmetry in gait cycle patterns. The evaluating can also include the motion evaluator 146 identifying amplitudes, periodicities, frequencies, and other characteristics of gait cycle patterns over time. The evaluating can also include comparing amplitudes, periodicities, frequencies, and other characteristics of multiple gait cycle patterns over time in any manner described herein. The evaluating can also include the motion evaluator 146 comparing the relative or absolute positions or distances between one or more gait locus points as described herein. The evaluating can also include identifying certain angles or other geometric metrics between two or more gait locus points in any manner described herein.

At step 712, the process includes the evaluation module 132 providing an evaluation of the subject based on the evaluating at step 710. For example, the evaluation module 132 can compare various cycle patterns and characteristics of the gait signatures of the subject determined by the evaluation engine 140 at step 710. The evaluation module 132 can also evaluate the relative or absolute positions or distances between gait locus points as determined at step 710. Overall, based on information identified, tracked, calculated, evaluated, and stored over steps 704, 706, 708, and 710, the evaluation module 132 can provide an evaluation of a subject, possibly including the identification of likely sources of lameness or other health conditions of the subject at step 712. The sources of lameness can be identified as being associated with certain anatomical features of the subject as described herein, and those sources can be identified in one or more reports generated by the evaluation module 132.

The evaluation provided by the evaluation module 132 can be organized in any suitable fashion, such as in one or more reports. In one embodiment, the evaluation engine 140 can calculate a statistical similarity or deviation of one or more motions as compared to benchmark motions stored in the reference data 125. As described above, such benchmark motions can include one or more previously-stored motions exhibited by the same or different subjects, or motions developed specifically for the purpose of evaluation.

In addition, the evaluation module 132 can determine the nature (e.g., weightbearing or non-weightbearing), severity, and/or grade of lameness or other conditions by considering the similarity to or difference from benchmark levels, for example, and provide that information as part of the evaluation of the subject. The grade of lameness can be expressed in a report using a numerical scale, an alphabetical scale, a color scale, or according to any other suitable means of presentation.

Reports generated by the evaluation module 132 at step 712 can be stored in the data store 120, presented on a display for individuals, printed, e-mailed, etc. Individuals, such as veterinarians or other healthcare service providers, can reference the reports to determine an appropriate manner in which to assist subjects. The reports can be used as a secondary source to recognize lameness, confirm a diagnosis provided by a veterinarian, for example, or to tailor the protocols suggested by the veterinarian to assist subjects.

The flowchart in FIG. 7 shows an example of the functions and operation of the computing environment 100. The components described herein, including the computing environment 100, can be embodied in hardware, software, or a combination of hardware and software. If embodied in software, each element can represent a module or group of code that includes program instructions to implement the specified logical function(s). The program instructions can be embodied in the form of, for example, source code that includes human-readable statements written in a programming language or machine code that includes machine instructions recognizable by a suitable execution system, such as a processor in a computer system or other system. If embodied in hardware, each element can represent a circuit or a number of interconnected circuits that implement the specified logical function(s).

The computing environment 100 can include at least one processing circuit. Such a processing circuit can include, for example, one or more processors and one or more storage or memory that are coupled to a local interface. The local interface can include, for example, a data bus with an accompanying address/control bus or any other suitable bus structure. Similarly, the computing device 160 can include at least one processing circuit. Such a processing circuit can include, for example, one or more processors and one or more storage or memory devices that are coupled to a local interface.

The storage or memory devices can store data or components that are executable by the processors of the processing circuit. For example, the management service 30 and/or other components can be stored in one or more storage devices and be executable by one or more processors in the computing environment 100. Similarly, the content processing engine 130, evaluation module 132, evaluation engine 140, and/or other components can be stored in one or more storage devices and be executable by one or more processors in the computing environment 100.

The content processing engine 130, evaluation module 132, evaluation engine 140, and/or other components described herein can be embodied in the form of hardware, as software components that are executable by hardware, or as a combination of software and hardware. If embodied as hardware, the components described herein can be implemented as a circuit or state machine that employs any suitable hardware technology. The hardware technology can include, for example, one or more microprocessors, discrete logic circuits having logic gates for implementing various logic functions upon an application of one or more data signals, application specific integrated circuits (ASICs) having appropriate logic gates, programmable logic devices (e.g., field-programmable gate array (FPGAs), and complex programmable logic devices (CPLDs)).

Also, one or more or more of the components described herein that include software or program instructions can be embodied in any non-transitory computer-readable medium for use by or in connection with an instruction execution system such as, a processor in a computer system or other system. The computer-readable medium can contain, store, and/or maintain the software or program instructions for use by or in connection with the instruction execution system.

A computer-readable medium can include a physical media, such as, magnetic, optical, semiconductor, and/or other suitable media. Examples of a suitable computer-readable media include, but are not limited to, solid-state drives, magnetic drives, or flash memory. Further, any logic or component described herein can be implemented and structured in a variety of ways. For example, one or more components described can be implemented as modules or components of a single application. Further, one or more components described herein can be executed in one computing device or by using multiple computing devices.

Further, any logic or applications described herein, including the content processing engine 130, evaluation module 132, evaluation engine 140, and/or other components can be implemented and structured in a variety of ways. For example, one or more applications described can be implemented as modules or components of a single application. Further, one or more applications described herein can be executed in shared or separate computing devices or a combination thereof. For example, a plurality of the applications described herein can execute in the same computing device, or in multiple computing devices. Additionally, terms such as "application," "service," "system," "engine," "module," and so on can be used interchangeably and are not intended to be limiting.

The above-described examples of the present disclosure are merely possible examples of implementations set forth for a clear understanding of the principles of the disclosure. Many variations and modifications can be made without departing substantially from the spirit and principles of the disclosure. All such modifications and variations are intended to be included herein within the scope of this disclosure and protected by the following claims.

Disjunctive language, such as the phrase "at least one of X, Y, or Z," unless specifically stated otherwise, is to be understood with the context as used in general to present that an item, term, etc., can be either X, Y, or Z, or any combination thereof (e.g., X, Y, and/or Z). Thus, such disjunctive language is not generally intended to, and should not, imply that certain embodiments require at least one of X, at least one of Y, or at least one of Z to be each present.

The above-described embodiments are merely possible examples of implementations to set forth for a clear understanding of the concepts of telemedical evaluation. Many variations and modifications can be made to the above-described embodiments without departing substantially from the spirit and principles of the disclosure. All such modifications and variations are intended to be included herein within the scope of this disclosure and protected by the following claims.

Therefore, at least the following is claimed:

1. A telemedical evaluation method, comprising:
    receiving a video comprising a number of frames of a subject in motion;
    identifying a species of the subject;
    identifying a plurality of anatomical features of the subject based on the species of the subject;
    determining a gait cycle pattern for individual ones of the plurality of anatomical features of the subject by tracking motion of the individual ones of the plurality of anatomical features in the video over at least a portion of the number of frames of the video;
    evaluating a first gait cycle pattern to identify lameness in one end of the subject based on a first amplitude over a first period of the first gait cycle pattern that is different than a second amplitude of a second period of the first gait cycle pattern;
    comparing at least a portion of the first gait cycle pattern to at least a portion of a second gait cycle pattern to further identify the lameness at one side of the one end of the subject; and
    providing an evaluation of the subject in the video based on the lameness in the one side of the one end of the subject.

2. The telemedical evaluation method of claim 1, further comprising stabilizing the video before determining the gait cycle pattern for the individual ones of the plurality of anatomical features of the subject.

3. The telemedical evaluation method of claim 1, wherein:
    the species of the subject is Equidae; and
    identifying the plurality of anatomical features of the subject comprises identifying at least two of withers, croup, fetlock, or hock of the subject.

4. The telemedical evaluation method of claim 1, further comprising determining a gait cycle pattern each of the plurality of anatomical features of the subject.

5. The telemedical evaluation method of claim 1, further comprising identifying asymmetry in the first gait cycle pattern.

6. The telemedical evaluation method of claim 1, wherein the evaluating further comprises identifying the lameness in the one end of the subject based on which anatomical feature of the subject is associated with the first gait cycle pattern.

7. The telemedical evaluation method of claim 1, further comprising determining lameness in a limb at the one side of the one end of the subject based on a correlation between at least one of the first period of the first gait cycle pattern or the second period of the first gait cycle pattern and the second gait cycle pattern.

8. The telemedical evaluation method of claim 7, wherein the lameness comprises weight bearing lameness in the limb of the subject.

9. The telemedical evaluation method of claim 1, wherein the evaluation of the subject is further based on at least one benchmark range of motion of for the subject.

10. A system for telemedical evaluation, comprising:
    a memory device configured to store computer-readable instructions; and
    at least one computing device configured, through execution of the computer-readable instructions, to at least:
        receive content including at least one image of a subject;
        identify a plurality of anatomical features of the subject with reference to the content;
        determine a gait cycle pattern for individual ones of the plurality of anatomical features of the subject by tracking motion of the individual ones of the plurality of anatomical features in the content;
        evaluate a first gait cycle pattern to identify lameness in one end of the subject based on a first amplitude over a first period of the first gait cycle pattern that is different than a second amplitude of a second period of the first gait cycle pattern;
        compare at least a portion of the first gait cycle pattern to at least a portion of a second gait cycle pattern to further identify the lameness at one side of the one end of the subject; and
        provide an evaluation of the subject based on the lameness in the one side of the one end of the subject.

11. The system for telemedical evaluation of claim 10, wherein the content comprises a number of images of the subject captured at different times.

12. The system for telemedical evaluation of claim 10, wherein the at least one computing device is further configured to track motion of the plurality of anatomical features among a number of images of the subject in the content.

13. The system for telemedical evaluation of claim 10, wherein the at least one computing device is further configured to determine a gait cycle pattern, respectively, for each of the plurality of anatomical features of the subject.

14. The system for telemedical evaluation of claim 10, wherein the at least one computing device is further configured to identify asymmetry in the first gait cycle pattern.

15. The system for telemedical evaluation of claim 10, wherein the at least one computing device is further configured to identify the lameness in the one end of the subject based on which anatomical feature of the subject is associated with the first gait cycle pattern.

16. A telemedical evaluation method, comprising:
 determining a gait cycle pattern for individual ones of a plurality of anatomical features of a subject by tracking motion of the plurality of anatomical features in a video;
 evaluating a first gait cycle pattern to identify lameness in one end of the subject based on a first amplitude over a first period of the first gait cycle pattern that is different than a second amplitude of a second period of the first gait cycle pattern;
 comparing at least a portion of the first gait cycle pattern to at least a portion of a second gait cycle pattern to further identify the lameness at one side of the one end of the subject; and
 providing an evaluation of the subject in the video based on the lameness in the one side of the one end of the subject.

17. The telemedical evaluation method of claim 16, further comprising determining a gait cycle pattern for each of the plurality of anatomical features of the subject.

18. The telemedical evaluation method of claim 16, further comprising identifying asymmetry in the first gait cycle pattern.

19. The telemedical evaluation method of claim 16, further comprising stabilizing the video before determining the gait cycle pattern for the individual ones of the plurality of anatomical features of the subject.

20. The telemedical evaluation method of claim 16, wherein the evaluation of the subject is further based on at least one benchmark range of motion of for the subject.

* * * * *